(12) United States Patent
Gilbert et al.

(10) Patent No.: US 6,772,071 B2
(45) Date of Patent: Aug. 3, 2004

(54) ESTIMATION OF TOXIC SUBSTANCE RELEASE

(75) Inventors: Ernest J. Gilbert, Simi Valley, CA (US); Shahryar Khajehnajafi, Thousand Oaks, CA (US)

(73) Assignee: Techtrac Systems, LLC, Camarillo, CA (US)

( * ) Notice: Subject to any disclaimer, the term of this patent is extended or adjusted under 35 U.S.C. 154(b) by 0 days.

(21) Appl. No.: 10/098,685

(22) Filed: Mar. 15, 2002

(65) Prior Publication Data

US 2002/0169557 A1 Nov. 14, 2002

Related U.S. Application Data

(60) Provisional application No. 60/284,750, filed on Apr. 18, 2001, and provisional application No. 60/312,429, filed on Aug. 15, 2001.

(51) Int. Cl.[7] .................................................. G01W 1/00
(52) U.S. Cl. ............................ 702/23; 73/23.2; 702/3
(58) Field of Search ................................. 702/2, 3, 182, 702/23; 73/40, 23.2, 31.02; 340/632; 700/266; 370/94.1

(56) References Cited

U.S. PATENT DOCUMENTS

| | | | |
|---|---|---|---|
| 5,132,968 A | | 7/1992 | Cephus ..................... 370/94.1 |
| 5,297,421 A | | 3/1994 | Hosonuma et al. ........... 73/40 |
| 5,468,964 A | * | 11/1995 | Gopalsami et al. ......... 250/393 |
| 5,604,299 A | | 2/1997 | Cobb ....................... 73/31.02 |
| 5,724,255 A | * | 3/1998 | Smith et al. ................ 700/266 |
| 5,832,411 A | | 11/1998 | Schatzmann et al. ......... 702/23 |
| 6,252,510 B1 | | 6/2001 | Dungan ..................... 340/632 |
| 6,295,859 B1 | * | 10/2001 | Hayden et al. .............. 73/23.2 |
| 6,385,558 B1 | | 5/2002 | Schlemm .................... 702/182 |
| 6,415,646 B1 | | 7/2002 | Kessel et al. ................ 73/23.2 |

OTHER PUBLICATIONS

Instruction manual entitled "Back Calculation," by the present assignee (SAFER Systems, LLC) more than one year before the priority date of the present patent application.

Product brochure entitled "Real–Time, Integrated Software for Chemical Emergency Management," by the present assignee (SAFER Systems, LLC), Oct., 1997.

Product brochure entitled "Your Future Can be SAFER," by a predecessor (DuPont) of the present assignee (SAFER Systems, LLC), Oct., 1989.

* cited by examiner

*Primary Examiner*—John Barlow
*Assistant Examiner*—Victor J. Taylor
(74) *Attorney, Agent, or Firm*—Christie, Parker & Hale, LLP (57) ABSTRACT

A system and method for estimating an amount of substance released into an ambient thereby creating a plume includes at one sensor adapted to be positioned at the plume and making multiple concentration measurements of the released substance at multiple times. A computer-based analyzer system is programmed with an algorithm. The analyzer receives concentration measurements from the at least one sensor and the algorithm generates an estimate of amount of substance released as a function of the multiple concentration measurements and the time of the measurements.

59 Claims, 5 Drawing Sheets

ESTIMATION OF TOXIC SUBSTANCE RELEASE

CROSS-REFERENCE TO RELATED APPLICATIONS

This application claims priority from U.S. provisional patent application Ser. No. 60/284,750, filed on Apr. 18, 2001, and U.S. provisional patent application Ser. 60/312,429, filed on Aug. 15, 2001, the disclosures of which are hereby incorporated herein by reference in their entirety.

BACKGROUND OF THE INVENTION

This invention relates generally to techniques for estimating the amount of release, or release rate, of a substance and, more particularly, to release of a toxic chemical. More particularly, the invention relates to estimating release of a toxic chemical in a liquid or gaseous state. The invention may be used to direct emergency response to an unfolding of the event, as well as to a post-event analysis or a pre-event preparation. The invention may be applied to fixed release locations, such as chemical facilities, as well as to portable events, such as may occur at a railroad car, a pipeline, or the like.

A significant challenge in any emergency scenario is the estimation of the amount of chemical being released. The impacted area to which the emergency responder is interested to know, in order to devise an escape route or evacuation zone or shelter in place, depends on the amount of chemical release, among other parameters. Therefore, having a good estimation of the release is very important.

An exemplary event may involve several derailed railroad cars leaking unknown amounts of chemical, or a plant process area engulfed in a toxic material with no way of observing where in the process the leak is occurring and how much chemical is being released. Each event is unique and may involve a very small amount of material, or be catastrophic in its scope. Initial estimates are very difficult and even an expert responder can only guess at the initial release. Therefore, a quick and accurate estimation of the release is crucial for the response agencies in warning the public and taking them out of harms way.

Existing release rate estimation schemes work best at fixed facilities that have solid process review programs and whose personnel clearly understand the highest probabilities for a release to occur. Events, of course, are not limited to fixed facilities, but can also be transportation-based, such as a railroad tank or car, barge, truck, or it can be in the form of a pipeline. With the wide range of chemical species that could be involved and the endless release possibilities, having techniques for quickly assessing the event is important. While known systems provide useful information about an event, they do not provide an assessment of the release for a significant portion of the duration of the event nor do they take into account the significance of changing meteorology.

SUMMARY OF THE INVENTION

The goal of the invention is to improve the accuracy of the amount of a chemical entering the ambient, and resulting impact area from the release, and to improve the speed of obtaining results in order to enhance response effort.

A method of estimating an amount of substance being released into an ambient, thereby creating a plume, includes making concentration measurements of the substance over a period of time and providing an estimate of the amount of the substance released as a function of the multiple concentration measurements and a time of the measurements. The method may further include considering atmospheric conditions of the ambient into which the substance was released. The considering of atmospheric conditions may include considering atmospheric conditions over the period of time. The considering of atmospheric conditions may include providing at least one weather sensor adapted to measure atmospheric conditions of the ambient into which the substance was released. The considering of atmospheric conditions may include downloading weather data from a global electronic network, downloading weather data from a government dial-up weather service, and/or estimating weather by a weather professional.

The estimate of the amount of substance released may be performed manually, such as by a person sensing that a plume can be detected by odor, or the like, or may be made by one or more sensors that are adapted to measure a concentration of the substance. If a sensor is used, the sensor may be a stationary sensor or a portable sensor. If a portable sensor is used, the portable sensor may be a wireless sensor. Furthermore, the portable sensor may be positioned at the beginning of the substance released, such as downwind of the release location. The portable sensors may be moved during the event. If so, attempts to collect data would resume after the move.

A determination may be made that a particular measurement is a valid measurement and projecting that particular measurement back in time in order to obtain a concentration measurement prior to the valid measurement being obtained. The measurement may be projected back in time to when the sensor was first impacted by the plume. Furthermore, measurements from a sensor may be no longer used when the sensor has reached a maximum measurement for the capabilities of the sensor.

A predicted profile of time and concentration measurements may be provided and the concentration measurements compared with the predicted profile. The predicted profile may be revised in response to the outcome of comparing. The algorithm may be performed until convergence with the predicted profile has occurred. Multiple measurements may be made in each of multiple different locations and an estimate of the amount of the substance released may be obtained as a function of the multiple concentration measurements at each of the locations and a time of the measurements.

A substance release rate estimation system for estimating an amount of substance released from a plume created by the release, according to another aspect of the invention, includes at least one sensor, an atmospheric conditions input, and a computer system that is programmed with an algorithm. The at least one sensor is positioned at the plume and measures concentration of the released substance. The atmospheric conditions input is adapted to input atmospheric conditions. The computer system receives concentration measurements from the sensor and atmospheric conditions from the atmospheric conditions input. The algorithm generates an estimate of a substance released from the concentration measurements and the atmospheric conditions.

A substance release estimation system for estimating an amount of released substance whose release creates a plume, according to another aspect of the invention, includes at least one sensor and a computer system programmed with an algorithm. The at least one sensor is adapted to be positioned at a plume and makes multiple concentration measurements of the released substance over time. The computer system receives concentration measurements from the at least one sensor. The algorithm generates an estimate of substance release from multiple ones of the concentration measurements that are obtained from the at least one sensor over time.

These and other objects, advantages and features of this invention will become apparent upon review of the following specification in conjunction with the drawings.

DESCRIPTION OF THE PREFERRED EMBODIMENT

Figure 1:
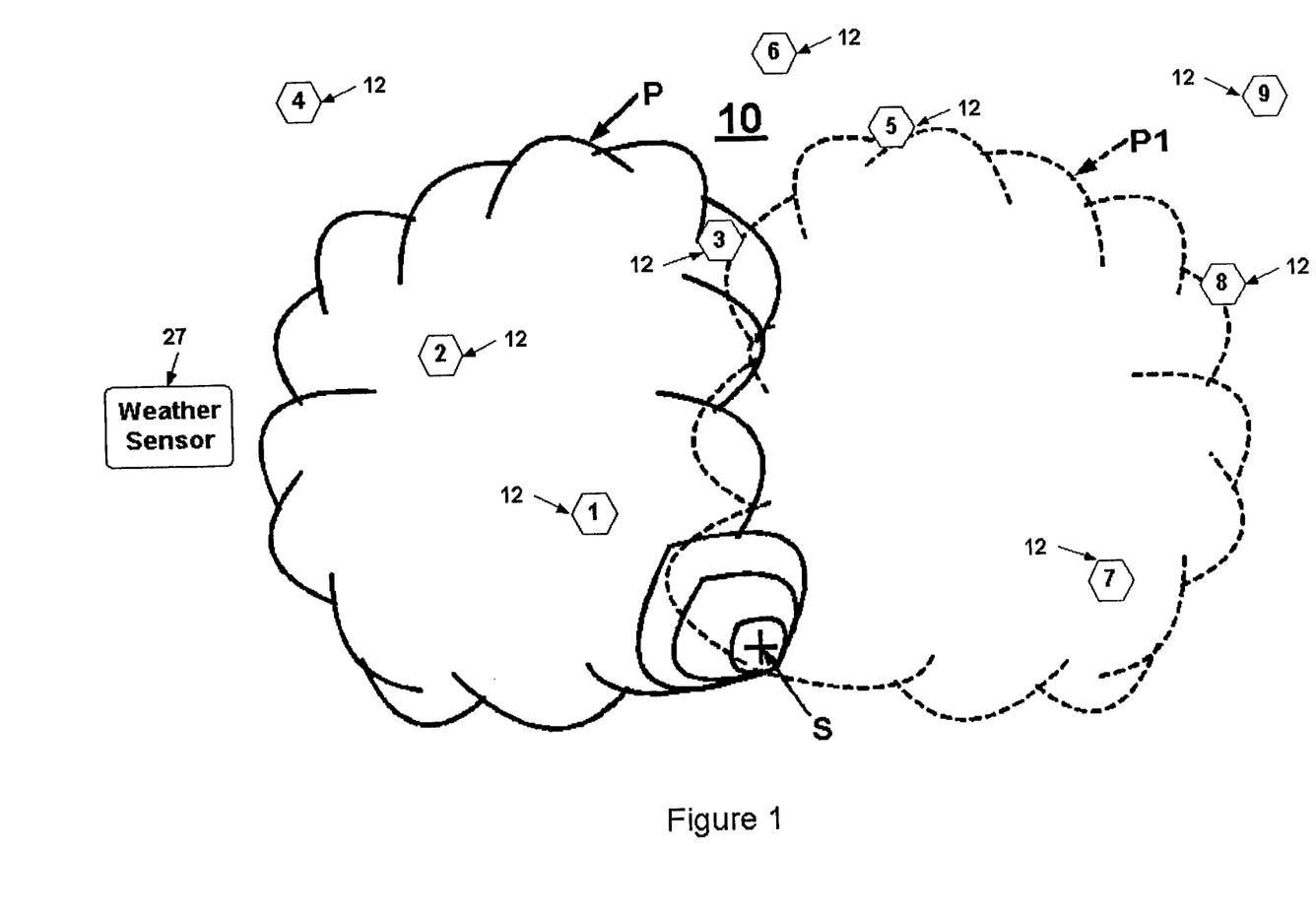
FIG. 1 is a top plan view of a plume generated by a release of a toxic substance and placement of sensors illustrating how plume evolution can change with prevailing weather conditions at the impact area.

Referring now specifically to the drawings, and the illustrative embodiments depicted therein, a substance release estimating system 10 including a plurality of sensors 12, shown in a random placement, are illustrated as measuring concentration of a plume P created by a chemical discharge at a release site S. Plume P is typically made up of a gas cloud from a liquid or gas chemical release. Plume P would typically be a toxic gas cloud that is usually not visible. In some circumstances, the cloud may be visible. The plume may change during the course of a release event, as illustrated by plume P1 in FIG. 1. Therefore, some sensors may not begin reading a concentration of the substance until later in an event while other sensors begin reading concentration early in an event and may saturate, or reach a maximum upper limit of its reading range and these may change as the evolution of the plume changes, such as by passage of time or by change in prevailing wind. The use of the term "toxic" herein may include chemicals that are harmful to plants, animals or humans, or explosive or flammable, or corrosive, or otherwise requiring a response from emergency personnel.

Substance release estimating system 10 includes a computer (not shown) running an algorithm 14 (FIG. 5) and one or more sensors 10. Information passed from each sensor may include a sensor ID number, its location, a time of making a reading, and a concentration measurement. This information is passed to algorithm 14. The algorithm is apprised of the sensor properties of each sensor, such as the type of chemical it can measure, the concentration at which it saturates, i.e., its maximum measurement, and any other relevant information. Sensors may be fixed sensors 12f, which are designed to continuously monitor within or near the source of emission, such as a plant S. The sensor network may be hard-wired to the computer running algorithm 14 and may continuously make sensor readings available. This may be utilized to provide an automatic data entry system.

Measurements may also be taken by portable gas sensors 12p placed in the release. A responder or detection vehicle may be placed downwind of the source of emission S and use radio telemetry and global position system (GPS) data to communicate to the computer running algorithm 14. This can also be thought of as an automatic data entry system. The portable sensors are positioned downwind of the release location. The sensor may be a wireless sensor that communicates with a central control by wireless communication or may be manually read. The portable sensor(s) may be positioned at the beginning of the substance release. Furthermore, the portable sensor(s) may be moved during the event. If so, attempts to collect data would discontinue during the move and resume after the move. The sensor(s) could data log the collected data to be used after an event. Also, fixed sensor(s) can be stand-alone or wired to a digital control system (DCS) or a process logic controller (PLC). The DCS or PLC converts the analog sensor output to a digital format useful to the computer. They may also store the data readings for use with other equipment and make the data available over a computer network or directly connected to the computer. Both the DCS and PLC would be polled by the algorithm 14.

A variety of gas monitoring techniques may be utilized, such as a photo-ionization detector (PID), a flame ionization detector (FID), an electrochemical detector, or the like. Measurements may also be taken by field personnel using hand-held portable measurement instruments downwind of the release. The concentration should be immediately relayed to the computer running algorithm 14, such as by telephone, radio, facsimile, or the like. This may be considered manual data entry. Subjective measurements may also be taken where the concentration is described by persons impacted by the event. A combination of some or all of the above sensing techniques may be utilized by algorithm 14.

Figure 2:
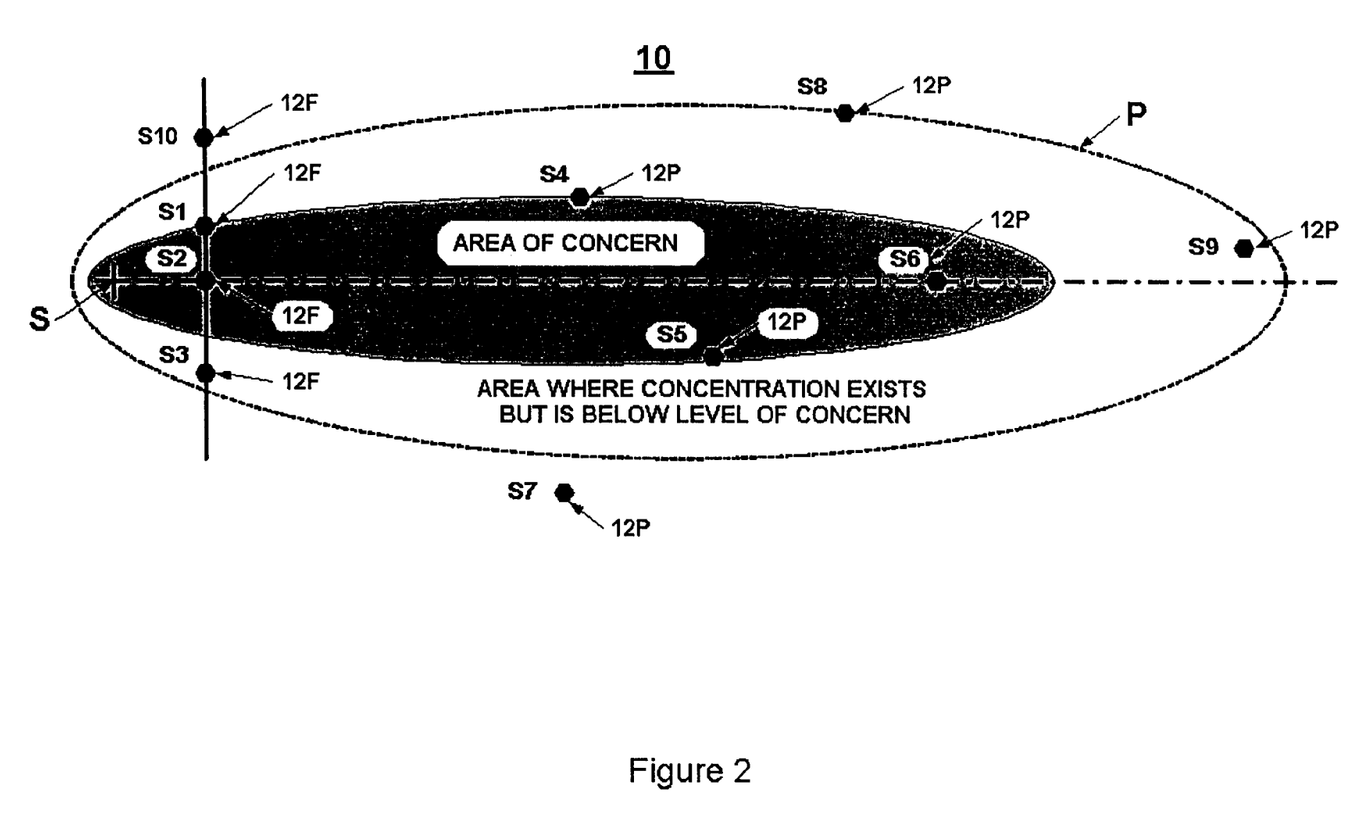
FIG. 2 is an idealized representation of a toxic substance release.

FIG. 2 represents an idealistic representation of a plume P. Plume P is idealistically made up of a central area of concern which may be, by way of example, a beginning of human toxicity, or explosive concentration, or other such level of concentration. The area outside of the area of concern, but within plume P, is an area where concentration will be processed by algorithm 14, but may not necessarily be the lowest level that can be measured. The outer area of plume P represents the area where some level of the cloud may be monitored at a range below the level of concern. As previously set forth, sensors 12f are full-time gas concentration monitors, typically a part of a digital control system, and are designated sensors S1, S2, S3, S10, on the FIG. 2. Sensors 12p are portable sensor monitors and must be deployed. Sensors S4, S5, S6, S7, S8 and S9 are portable sensors. Some gas-monitoring sensors may take up to a fixed period of time, such as 50 seconds for example, to start detecting the chemical. This is known as monitoring lag or sensor lag. In most cases, once a reading starts, it continues being available for the entire event unless the sensor becomes saturated. Alternatively, a reading can be taken once at a location using hand-held devices and a voice reporting the measurement, time, and location back to the control running algorithm 14.

Figure 3:
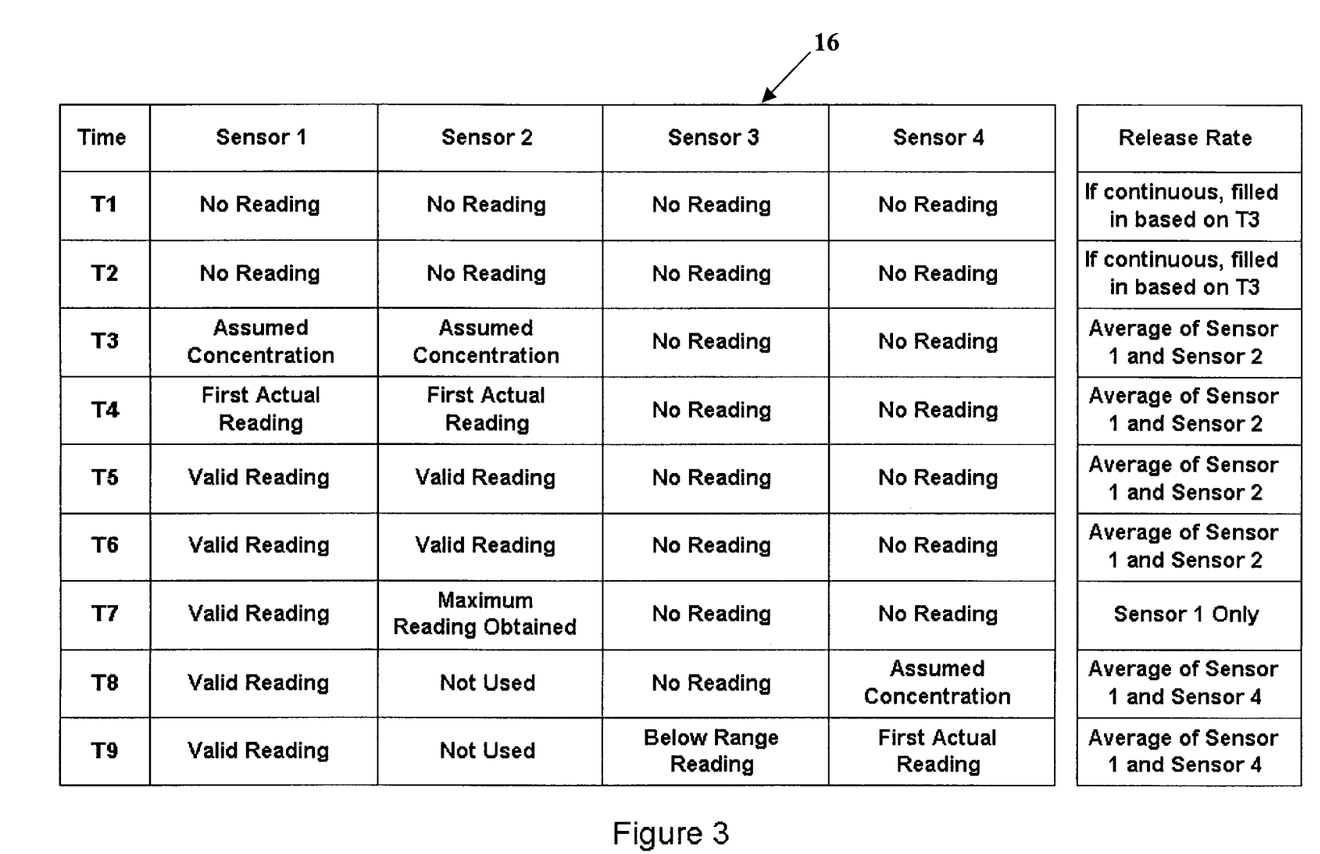
FIG. 3 is a chart illustrating sensor response during different time intervals during an episode.

Referring to FIG. 3, a numbers array 16 shows the manner in which readings are handled for each sensor (sensors 1–4 are illustrated) during an event which is divided into intervals T1, T2 . . . T9. Intervals T1–T9 are illustrative only. Fewer or additional intervals may be utilized. Once the algorithm is run on intervals T1–T9, the algorithm may be repeated again. In the illustrative embodiment, each interval T1–T9 is approximately 60 seconds, although other intervals may be utilized.

At time T1, the event begins. Time T3 is the first time that sensors 1 and 2 begin to be affected by the released substance. It may take an additional period of time, for example, 60 seconds, to obtain a concentration reading due to sensor lag. At time T4, sensors 1 and 2 obtain an actual concentration reading. Algorithm 14 fills in a concentration value for interval T3 for both sensors 1 and 2 that relate to the actual concentration reading made at interval T4. In the illustrative embodiment, the algorithm fills in a concentration reading at interval T3 which is the same as a concentration-reading read for sensors 1 and 2 in interval T4. At interval T7, sensor 2 obtains a reading that is a maximum reading for the type of instrument that is sensor 2. Because this represents a saturation of sensor 2, readings from sensor 2 are not used beyond interval T7 because they may be inaccurate. However, sensor 1 continues to obtain valid readings through interval T9. At interval T8, sensor 4 begins to get a reading, but not a reliable reading. However, at interval T9, sensor 4 obtains a valid reading which is assumed by algorithm 14 to have occurred in interval T8 even though the sensor could not obtain a reliable reading at interval T8. The intervals in which a valid reading are projected back in time are a function of the physical characteristics of the sensor and are established by the lag time between obtaining a reading and obtaining a reliable reading. In interval T9, sensor 3 begins to get a reading, but it is not yet reliable.

The manner in which the readings in array 16 are used is shown in the separate column at the right in FIG. 3. From intervals T3–T6, sensors 1 and 2 were used for calculation of substance estimated release. In interval T7, sensor 1 was used for release rate calculation. From intervals T8–T9, sensors 1 and 4 were used for the calculation in algorithm 14. This technique can be used for as many sensors as can participate based upon valid measurement range. The program can be run over and over again as long as the event continues until the release is stopped. Once the release is stopped, the algorithm may continue to monitor concentration and compare the plume to the expected concentrations as set forth below in order to obtain mathematical convergence as will be discussed in more detail below.

Figure 4A:
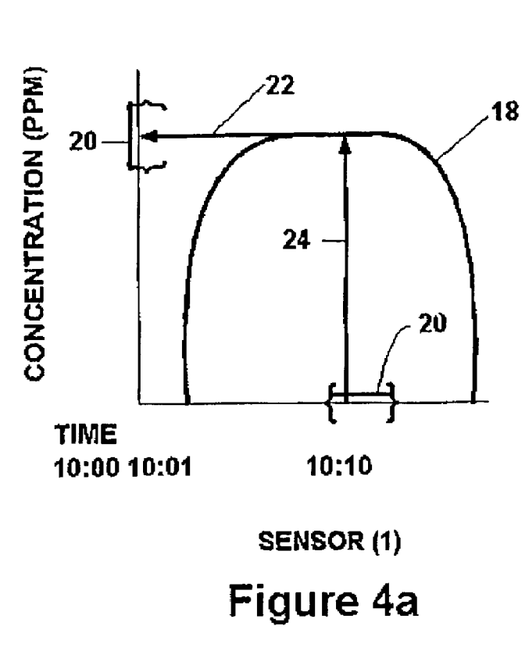
FIGS. 4a–4c illustrate an algorithm useful with the present invention.
Figure 4B:
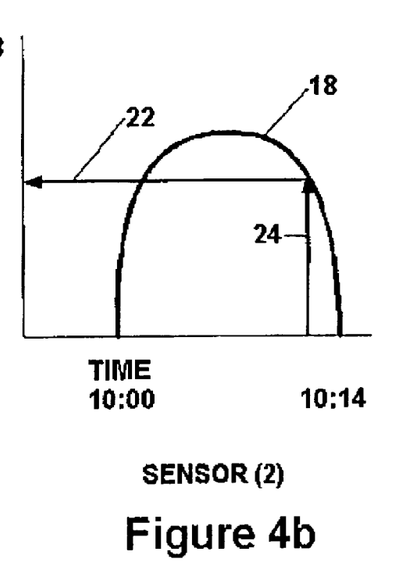
Figure 4C:
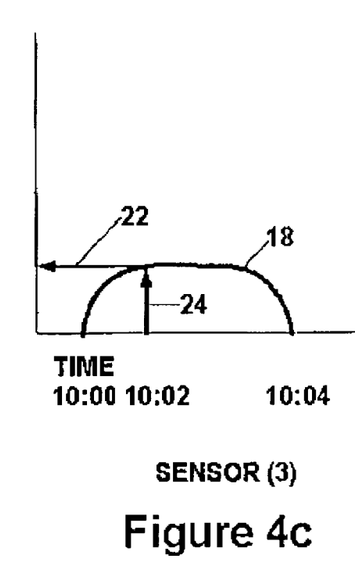

Algorithm 14, in the illustrative embodiment, runs a dispersion model with a guessed, or assumed, or predicted, or trial, value for release rate. Algorithm 14 produces a time profile 18 for each sensor (FIGS. 4a–4c). Actual sensor information, namely, sensor time and concentration measurement, is matched against the predicted profile. A determination is made whether there is a match within a particular convergence span 20. If there is a match within the convergence span in terms of time and concentration measurement for all sensors, the predicted value is recorded as the true value. Otherwise, a new predicted profile is tried. Actual concentration value is indicated by line 22. Actual time value is indicated by line 24. There are two loops for convergence; one loop converges on the time parameter and the other converges on the concentration parameter. When both the time and concentration parameters are converged within a tolerance limit, the computed value is accepted.

The trial method would basically establish limits for the release rate or amount, and then use one of a root-finding method, such as Bisection Newton-Raphson, false position, or the like, to find an actual release rate or release amount. After this procedure is complete, a release rate versus time is obtained for the source S which is then fed to the dispersion model for chemical impact. This procedure is repeated as new information is received and updates are determined. Accuracy is greater for measurements taken closer to the centerline C of the plume (FIG. 2) and for readings that are not too close and not too far from the release point S.

To speed up the algorithm, a weight factor may be applied. The value of this weight factor may change, for example, by 0.1 from measurements taken from the plume centerline to measurements on the edge of the cloud. Therefore, if a tolerance value of 1% is set for the centerline concentration accuracy, the edge measurement may only require a 10% accuracy. This may be accomplished by assigning a weight factor to each sensor as a function of its position. During the iteration, these weight factors can be used to determine convergence criteria for each sensor.

A convergence criteria may be:

$$\frac{|C_{meas} - C_{est}|}{C_{meas}} < \frac{TOL}{W_n} \quad (1)$$

where $C_{meas}$=measured concentration $C_{est}$=estimated concentration

TOL=tolerance $W_n$=weight factor for each sensor wherein $W_n$ is between 0.1 and 1.

After the criteria in equation 1 for each sensor is met, the program will complete and report the release rate.

Figure 5:
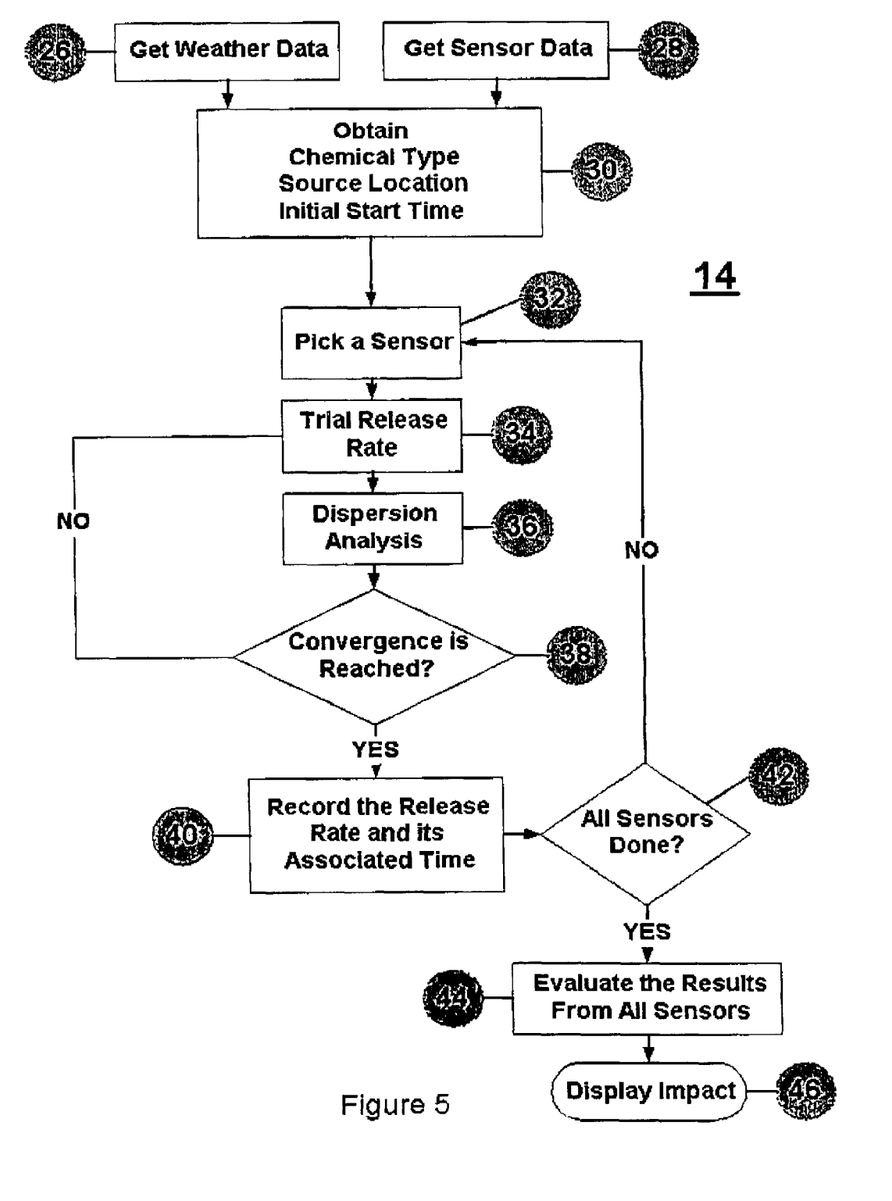
FIG. 5 is a flowchart of a control program, according to the invention.

Algorithm 14 begins by obtaining weather data 26 and sensor data at 28 from the various sensors 12. Weather data may be obtained from a weather sensor 27. Alternatively, weather data could be obtained from a global electronic network, such as the Internet, government dial-up services, other companies' fixed systems, wireless portable weather sensors, or estimated by a weather professional, or the like. At 30, the algorithm determines the chemical that is being detected. It assumes that the chemical corresponds with the type of sensor that is detecting something. In other words, if a sensor for a particular chemical is sensing a condition, we assume that it is that chemical that is source of the toxic release. The algorithm 14 can change that conclusion if it is later on determined to be incorrect.

At 32, the algorithm picks one of the sensors and at 34 picks a trial, or predicted, release rate. A dispersion analysis is run at 36 and it is determined at 38 whether convergence has been reached. If it is determined at 38 that convergence has not been reached, then a new predicted release rate is chosen at 34 and the dispersion analysis is repeated at 36 until it is determined at 38 that convergence has been reached. When it is determined at 38 that convergence has been reached, the release rate and its associated times are recorded at 40. When it is determined at 42 that all sensors 12 are processed in this manner, the release rate calculations for all sensors are evaluated at 44. This may be accomplished by estimating a release rate by the back calculation model for each measured concentration, along with its time of measurement shown in FIG. 3. An adjustment on each concentration at each time is made to account for the cloud travel time from source to measuring location. These time-stamped rates would then be sorted in ascending order of time before it is passed on to the dispersion model for the overall plume impact. An estimated rate for the earliest recorded time would be used from the time beginning with the release. An arithmetic average release rate may be used for rates calculated at identical times. If the release rate readings from the sensors are consistent with valid release rate readings, the readings are combined utilizing a known statistical process and the impact of the release rate is displayed at 46 on a monitor, or the like.

Substance release estimation system 10 allows an estimation of the amount of toxic chemical released as the event occurs. Furthermore, the system is capable of being highly automated which removes the skill of the operator from the analysis. Moreover, the substance release estimation system can be used as a monitoring system by taking into account time as a factor in the measurements such that the system may be utilized to alert the operator of the occurrence of an event rather than the other way around. In the illustrative embodiment, portable sensors 12P may be of the type manufactured by Rae Systems, a wireless gas detection system manufactured by Gastronics, or other commercially available wireless gas detection system. Utilizing substance release estimation system 10, as data is changed, the result is updated. During an interval, such as 10 minutes, data is updated automatically. The plume may be continuously regenerated as more and more data is obtained.

Substance release estimation system 10 may make a record of the event for review after the event by interested parties. The system can be utilized for monitoring installations, especially where fixed sensors are placed. Portable sensors can be placed in downwind locations where movement of the plume is expected. Monitoring movement of the plume is assisted by the automatic entry of atmospheric conditions as is possible with substance release estimation system 10. The present invention works well with any existing dispersion modeling known in the art. This may include the REAL-TIME™ system marketed by the present assignee, SAFER Systems, L.L.C., the ALOHA system supplied by the United States Government, the CHARM system supplied by Radiant Corporation, the COMPAS system supplied by Brank Software Systems, or the like. Such dispersion models are based upon a mass balance around the release site, but other dispersion model basis may be used.

Substance release estimation system utilizes a) gas detection sensors, b) meteorological measurement, c) release location information, d) starting time of the release and d) dispersion model. Examples of types of sensors useful with system 10 include PID, electro-chemical, paper tape, open path, and the like. The location of the sensor may be verbally described or measured with global position accuracy. Time of measurement, as well as upper and lower limits of concentration measurement, are taken into account, as well as the chemical of response or what substances can be accurately measured. Meteorological measurement may include wind speed and direction, as well as stability classification as defined by the Environmental Protection Agency (EPA). Release location is the actual source of the release.

Substance release estimation system 10 may be a standalone system or may be incorporated into other programs. As previously set forth, system 10 may be utilized for dispersion modeling, providing assistance as an event unfolds, reconstruction of the unfolding of the event after the fact, and monitoring of equipment for the occurrence of a release. Although illustrated for use with toxic liquid or gas chemicals, the substance release estimation system 10 could also be used to track non-toxic chemical releases.

Changes and modifications in the specifically described embodiments can be carried out without departing from the principles of the invention which is intended to be limited only by the scope of the appended claims, as interpreted according to the principles of patent law including the doctrine of equivalents.

What is claimed is:

1. A method of estimating an amount of a substance being released into a surrounding medium thereby creating a plume, comprising:

making multiple concentration measurements of the substance at multiple locations and at multiple times;

estimating a release rate of the substance released as a function of said multiple concentration measurements at said locations and said times of the measurements.

2. The method of claim 1 wherein said providing an estimate includes considering atmospheric conditions of the surrounding medium into which the substance was released.

3. The method of claim 2 wherein said considering atmospheric conditions includes considering atmospheric conditions at said times.

4. The method of claim 2 wherein said considering atmospheric conditions includes providing at least one weather sensor adapted to measure atmospheric conditions of the surrounding medium into which the substance was released.

5. The method of claim 2 wherein said considering atmospheric conditions includes downloading weather data from a global network.

6. The method of claim 2 wherein said considering atmospheric conditions includes downloading weather data from a government dial-up weather service.

7. The method of claim 2 wherein said considering atmospheric conditions includes estimating weather by a weather professional.

8. The method of claim 1 wherein said making concentration measurements comprises providing at least one sensor that is adapted to measure a concentration of the substance and positioning said at least one sensor where it is predicted that said at least one sensor will come into contact with the plume.

9. The method of claim 8 wherein said at least one sensor is a sensor chosen from a stationary sensor and a portable sensor.

10. The method of claim 9 wherein said at least one sensor is a wireless portable sensor.

11. The method of claim 9 wherein said at least one sensor is a portable sensor and including repositioning said at least one sensor during the release of the substance.

12. The method of claim 11 including discontinuing measurements during said repositioning and resuming making measurements after said repositioning.

13. The method of claim 9 wherein said at least one sensor is a portable sensor and including positioning said portable sensor at a beginning of the substance release.

14. The method of claim 8 including determining that a particular measurement with a particular one of said at least one sensor is a valid measurement and projecting said particular measurement to a prior period in time to obtain a concentration measurement for said particular one of said at least one sensor prior to said valid measurement.

15. The method of claim 14 including projecting said particular measurement to a prior period in time to when said particular one of said at least one sensor first was impacted by the plume.

16. The method of claim 8 including determining that a particular measurement with a particular one of said at least one sensor is a maximum measurement and not using future measurements with said particular one of said at least one sensor that occur after said maximum measurement.

17. The method of claim 1 wherein said estimating includes providing a predicted profile of time and concentration measurements and comparing said concentration measurements with the predicted profile.

18. The method of claim 17 including revising said predicted profile in response to said comparing.

19. The method of claim 18 including determining that the concentration measurements have converged with the predicted profile.

20. A method of estimating an amount of a substance being released into a surrounding medium thereby creating a plume, comprising:
  making multiple concentration measurements of the substance at multiple different locations and at multiple times;
  estimating the amount of the substance released as a function of said multiple concentration measurements at said locations and times of the measurements; and
  wherein said estimating includes adjusting said measurements for travel time of the plume.

21. A substance release rate estimation system for estimating an amount of substance released from a plume created by the release, comprising:
  at least one sensor adapted to be positioned at the plume, said at least one sensor measuring concentration of the released substance;
  an atmospheric conditions input adapted to inputting atmospheric conditions of the surrounding medium into which the substance was released; and
  a computer-based analyzer being programmed with an algorithm, said analyzer receiving multiple concentration measurements from said at least one sensor at multiple times and atmospheric conditions from said atmospheric conditions input, said algorithm generating an estimate of a substance release rate from said concentration measurements and said atmospheric conditions.

22. The system of claim 21 wherein said atmospheric conditions input considers atmospheric conditions at said times.

23. The system of claim 21 wherein said atmospheric conditions input includes at least one weather sensor adapted to measure atmospheric conditions of the surrounding medium into which the substance was released.

24. The system of claim 21 wherein said atmospheric conditions input downloads weather data from a global network.

25. The system of claim 21 wherein said atmospheric conditions input downloads weather data from a government dial-up weather service.

26. The system of claim 21 wherein said atmospheric conditions input receives weather estimates from a weather professional.

27. The system of claim 21 wherein said at least one sensor is positioned where it is predicted that said at least one sensor will come into contact with a plume.

28. The system of claim 21 wherein said at least one sensor is a sensor chosen from a stationary sensor and a portable sensor.

29. The system of claim 21 wherein said at least one sensor is a wireless portable sensor.

30. The system of claim 29 wherein said at least one sensor is a portable sensor that is adapted to be repositioned during the release of the substance.

31. The system of claim 30 wherein said concentration measurements are suspended while said portable sensor is being repositioned and resumed after said repositioning.

32. The system of claim 21 wherein said at least one sensor is a portable sensor and is adapted to be positioned at a beginning of the substance release.

33. The system of claim 21 wherein said analyzer determines that a particular measurement with a particular one of said at least one sensor is a valid measurement and projecting said particular measurement to a prior period in time to obtain a concentration measurement for said particular one of said at least one sensor prior to said valid measurement.

34. The system of claim 33 wherein said analyzer projects said particular measurement to a prior period in time to when said particular one of said at least one sensor first was impacted by the plume.

35. The system of claim 21 said analyzer determines that a particular measurement with a particular one of said at least one sensor is a maximum measurement and not using future measurements with said particular one of said at least one sensor that occur after said maximum measurement.

36. The system of claim 21 wherein said algorithm generates said estimate by predicting a profile of time and concentration measurements and comparing said concentration measurements with the predicted profile.

37. The system of claim 36 wherein said algorithm revises said predicted profile in response to said comparing.

38. The system of claim 37 wherein said algorithm determines that the concentration measurements have converged with the predicted profile.

39. The system of claim 21 wherein multiple measurements are made in each of multiple different locations and the amount of the substance released is estimated as a function of said multiple concentration measurements at each of said locations and times of the measurements.

40. The system of claim 39 wherein said estimates are adjusted for travel time of the plume.

41. A substance release estimation system for estimating an amount of released substance, the release of which creates a plume, comprising:
  a plurality of sensors adapted to be positioned at multiple different locations with respect to plume and make multiple concentration measurements of the released substance at the different locations at multiple times; and
  a computer-based analyzer being programmed with an algorithm, said analyzer receiving concentration measurements from said plurality of sensors, said algorithm generating an estimate of a release rate of substance released from said concentration measurements.

42. The system of claim 41 including an atmospheric conditions input that considers atmospheric conditions at said times.

43. The system of claim 42 wherein said atmospheric conditions input includes at least one weather sensor adapted to measure atmospheric conditions of the surrounding medium into which the substance was released.

44. The system of claim 42 wherein said atmospheric conditions input downloads weather data from a global network.

45. The system of claim 42 wherein said atmospheric conditions input downloads weather data from a government dial-up weather service.

46. The system of claim 42 wherein said atmospheric conditions input receives weather estimates from a weather professional.

47. The system of claim 41 wherein said at least one sensor is positioned where it is predicted that said at least one sensor will come into contact with a plume.

48. The system of claim 41 wherein said at least one sensor is a sensor chosen from a stationary sensor and a portable sensor.

49. The system of claim 41 wherein said at least one sensor is a wireless portable sensor.

50. The system of claim 49 wherein said at least one sensor is a portable sensor that is adapted to be repositioned during the release of the substance.

51. The system of claim 50 wherein said concentration measurements are suspended while said portable sensor is being repositioned and resumed after said repositioning.

52. The system of claim 41 wherein said at least one sensor is a portable sensor and is adapted to be positioned at a beginning of the substance release.

53. The system of claim 41 wherein said analyzer determines that a particular measurement with a particular one of said at least one sensor is a valid measurement and projecting said particular measurement to a prior period in time to obtain a concentration measurement for said particular one of said at least one sensor prior to said valid measurement.

54. The system of claim 53 wherein said analyzer projects said particular measurement to a prior period in time to when said particular one of said at least one sensor first was impacted by the plume.

55. The system of claim 41 wherein said analyzer determines that a particular measurement with a particular one of said at least one sensor is a maximum measurement and not using future measurements with said particular one of said at least one sensor that occur after said maximum measurement.

56. The system of claim 41 wherein said algorithm generates said estimate by predicting a profile of time and concentration measurements and comparing said concentration measurements with the predicted profile.

57. The system of claim 56 wherein said algorithm revises said predicted profile in response to said comparing.

58. The system of claim 57 wherein said algorithm determines that the concentration measurements have converged with the predicted profile.

59. A substance release estimation system for estimating an amount of released substance, the release of which creates a plume, comprising:

at least one sensor adapted to be positioned at a plume and make multiple concentration measurements of the released substance at multiple times; and a computer-based analyzer being programmed with an algorithm, said analyzer receiving concentration measurements from said at least one sensor, said algorithm generating an estimate of amount of substance released from said concentration measurements;

wherein multiple measurements are made in each of multiple different locations and the amount of the substance released is estimated as a function of said multiple concentration measurements at each of said locations and times of the measurements;

wherein said estimates are adjusted for travel time of the plume.

* * * * *

UNITED STATES PATENT AND TRADEMARK OFFICE
CERTIFICATE OF CORRECTION

PATENT NO. : 6,772,071 B2
DATED : August 3, 2004
INVENTOR(S) : Gilbert et al.

It is certified that error appears in the above-identified patent and that said Letters Patent is hereby corrected as shown below:

<u>Column 10,</u>
Line 5, after "claim 21", insert -- wherein --.
Line 30, after "respect to", insert -- a --.

Signed and Sealed this

Fifteenth Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,772,071 B2
DATED : August 3, 2004
INVENTOR(S) : Gilbert et al.

It is certified that error appears in the above-identified patent and that said Letters Patent is hereby corrected as shown below:

<u>Title page,</u>
Item [57], ABSTRACT,
Lines 2-3, after "includes at", insert -- least --.

Signed and Sealed this

Twenty-eighth Day of March, 2006

JON W. DUDAS
*Director of the United States Patent and Trademark Office*